US009592297B2

(12) United States Patent
Xiang et al.

(10) Patent No.: US 9,592,297 B2
(45) Date of Patent: *Mar. 14, 2017

(54) ANTIBODY AND PROTEIN FORMULATIONS

(71) Applicant: Bayer HealthCare LLC, Whippany, NJ (US)

(72) Inventors: Jun Xiang, Pleasant Hill, CA (US); Xinghang Ma, Dublin, CA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 454 days.

This patent is subject to a terminal disclaimer.

(21) Appl. No.: 13/843,780

(22) Filed: Mar. 15, 2013

(65) Prior Publication Data

US 2014/0065159 A1 Mar. 6, 2014

Related U.S. Application Data

(63) Continuation-in-part of application No. 13/601,598, filed on Aug. 31, 2012, now Pat. No. 8,613,919.

(51) Int. Cl.

| | |
|---|---|
| ***A61K 39/395*** | (2006.01) |
| ***A61K 47/26*** | (2006.01) |
| ***C07K 16/38*** | (2006.01) |
| ***A61K 47/18*** | (2006.01) |
| ***A61K 47/22*** | (2006.01) |
| ***C07K 16/18*** | (2006.01) |
| *A61K 39/00* | (2006.01) |

(52) U.S. Cl.

CPC .......... *A61K 47/26* (2013.01); *A61K 39/3955* (2013.01); *A61K 39/39591* (2013.01); *A61K 47/183* (2013.01); *A61K 47/22* (2013.01); *C07K 16/18* (2013.01); *C07K 16/38* (2013.01); *A61K 2039/505* (2013.01); *C07K 2317/94* (2013.01)

(58) Field of Classification Search

None

See application file for complete search history.

(56) References Cited

U.S. PATENT DOCUMENTS

| | | | | |
|---|---|---|---|---|
| 4,075,193 | A | 2/1978 | Campbell | |
| 4,093,606 | A | 6/1978 | Coval | |
| 4,374,763 | A | 2/1983 | Takagi | |
| 4,499,073 | A | 2/1985 | Tenold | |
| 4,597,966 | A | 7/1986 | Zolton | |
| 4,816,567 | A | 3/1989 | Cabilly | |
| 4,877,608 | A | 10/1989 | Lee | |
| 5,096,885 | A | 3/1992 | Pearlman | |
| 5,217,954 | A | 6/1993 | Foster | |
| 5,580,856 | A | 12/1996 | Prestrelski | |
| 5,608,038 | A | 3/1997 | Eibl | |
| 5,654,403 | A | 8/1997 | Smith | |
| 5,792,838 | A | 8/1998 | Smith | |
| 5,804,557 | A | 9/1998 | Cleland | |
| 5,849,700 | A | 12/1998 | Sorenson | |
| 5,871,736 | A | 2/1999 | Bruegger | |
| 5,994,511 | A | 11/1999 | Lowman | |
| 6,165,467 | A | 12/2000 | Hagiwara | |
| 6,252,055 | B1 | 6/2001 | Relton | |
| 6,267,958 | B1 | 7/2001 | Andya | |
| 6,440,426 | B1 | 8/2002 | Wheeler | |
| 6,525,102 | B1 | 2/2003 | Chen | |
| 6,638,913 | B1 | 10/2003 | Speck | |
| 6,685,940 | B2 | 2/2004 | Andya | |
| 6,875,432 | B2 | 4/2005 | Liu | |
| 6,908,610 | B1 | 6/2005 | Sato | |
| 7,666,413 | B2 | 2/2010 | Liu | |
| 8,142,776 | B2 | 3/2012 | Liu | |
| 8,318,161 | B2 | 11/2012 | Esue | |
| 8,613,919 | B1 * | 12/2013 | Ma et al. | 424/130.1 |
| 2002/0045571 | A1 | 4/2002 | Liu | |
| 2003/0092607 | A1 | 5/2003 | Carpenter | |
| 2003/0092622 | A1 | 5/2003 | Sato | |
| 2003/0113316 | A1 | 6/2003 | Kaisheva | |
| 2003/0118583 | A1 | 6/2003 | Emery | |
| 2003/0138416 | A1 | 7/2003 | Lau | |
| 2003/0138417 | A1 | 7/2003 | Kaisheva | |
| 2003/0180287 | A1 | 9/2003 | Gombotz | |
| 2003/0190316 | A1 | 10/2003 | Kakuta | |
| 2004/0018200 | A1 | 1/2004 | Oliver | |
| 2004/0022792 | A1 | 2/2004 | Klinke | |
| 2004/0037803 | A1 | 2/2004 | Sato | |
| 2004/0038878 | A1 | 2/2004 | Tanikawa | |
| 2004/0191243 | A1 | 9/2004 | Chen | |
| 2004/0197324 | A1 | 10/2004 | Liu | |
| 2004/0228862 | A1 | 11/2004 | Shelton | |

(Continued)

FOREIGN PATENT DOCUMENTS

| | | | |
|---|---|---|---|
| EP | 0025719 | A2 | 3/1981 |
| EP | 0187712 | A2 | 7/1986 |

(Continued)

OTHER PUBLICATIONS

Arakawa et al. (1991). "Protein-Solvent Interactions in Pharmaceutical Formulations" Pharmaceutical Research 8(3):285-291.

Bam et al. (1995). "Stability of Protein Formulations: Investigation of Surfactant Effects by a Novel EPR Spectroscopic Technique," Pharmaceutical Research 12:2-11.

Bhambhani, et al.; "Formulation design and high-throughput excipient selection based on structural integrity and conformational stability of dilute and highly concentrated IgG1 monoclonal antibody solutions.", J Pharm Sci. Mar. 2012;101(3):1120-35.

Breen, E.D. et al. (Sep. 2001). "Effect of Moisture on the Stability of a Lyophilized Humanized Monoclonal Antibody Formulation," Pharmaceutical Research 18(9): 1345-1353.

Buzzell, et al.; "The effect of charge and ionic strength on the viscosity of ribonuclease"; J. Phys. Chem. 60:1204-1207 (1956).

Carpenter et al. (1997). "Rational Design of Stable Lyophilized Protein Formulations: Some Practical Advice," Pharmaceutical Research 14(8):969-975.

(Continued)

*Primary Examiner* — Yunsoo Kim

(57) ABSTRACT

Provided are salt-free antibody and other protein formulations that are substantially isosmotic and of low viscosity. Also provided are methods for the treatment of diseases using the disclosed formulations.

1 Claim, 2 Drawing Sheets

(56) References Cited

U.S. PATENT DOCUMENTS

| | | | |
|---|---|---|---|
| 2005/0004354 A1 | 1/2005 | Salfeld |
| 2005/0175603 A1 | 8/2005 | Liu |
| 2006/0034821 A1 | 2/2006 | Kline |
| 2006/0051347 A1 | 3/2006 | Winter |
| 2006/0127395 A1 | 6/2006 | Arvinte |
| 2006/0182740 A1 | 8/2006 | Yang |
| 2007/0020255 A1 | 1/2007 | Ueno |
| 2007/0053871 A1 | 3/2007 | Li |
| 2007/0053900 A1 | 3/2007 | Liu |
| 2007/0116700 A1 | 5/2007 | Liu |
| 2007/0122402 A1 | 5/2007 | Bolli |
| 2007/0184050 A1 | 8/2007 | Ishikawa |
| 2008/0071063 A1 | 3/2008 | Allan |
| 2009/0169544 A1 | 7/2009 | Nilsson |
| 2009/0169581 A1 | 7/2009 | Sandrine |
| 2009/0280129 A1 | 11/2009 | Liu |
| 2009/0291076 A1 | 11/2009 | Morichika |
| 2010/0158898 A1 | 6/2010 | Liu |
| 2010/0239567 A1 | 9/2010 | Esue |
| 2012/0064086 A1 | 3/2012 | Liu |

FOREIGN PATENT DOCUMENTS

| | | |
|---|---|---|
| EP | 0303746 A1 | 2/1989 |
| EP | 0303746 B1 | 11/1992 |
| EP | 0531539 A1 | 3/1993 |
| EP | 0597101 A1 | 5/1994 |
| EP | 0661060 A2 | 7/1995 |
| EP | 0787497 A2 | 8/1997 |
| EP | 0612251 B1 | 12/1997 |
| EP | 0841067 A1 | 5/1998 |
| EP | 0531539 B1 | 6/1998 |
| EP | 0303746 B2 | 12/1998 |
| EP | 0909564 A1 | 4/1999 |
| EP | 0661060 B1 | 5/2001 |
| EP | 1197221 A1 | 4/2002 |
| EP | 0841067 B1 | 5/2002 |
| EP | 1314437 | 5/2003 |
| EP | 1336410 | 8/2003 |
| EP | 1356829 A2 | 10/2003 |
| EP | 1475100 | 11/2004 |
| EP | 1475101 | 11/2004 |
| EP | 1977763 A1 | 10/2008 |
| EP | 1981824 | 10/2008 |
| EP | 2196476 A1 | 6/2010 |
| EP | 2335725 A1 | 6/2011 |
| WO | WO 89/11297 | 11/1989 |
| WO | WO 90/11091 | 10/1990 |
| WO | WO 97/04801 | 2/1997 |
| WO | WO 97/26862 | 7/1997 |
| WO | WO 97/26909 | 7/1997 |
| WO | WO 97/45140 | 12/1997 |
| WO | WO 98/22136 | 5/1998 |
| WO | WO 01/24814 | 4/2001 |
| WO | WO 01/64241 | 9/2001 |
| WO | WO 02/11753 | 2/2002 |
| WO | WO 02/13860 | 2/2002 |
| WO | WO 02/17957 | 3/2002 |
| WO | WO 02/30463 | 4/2002 |
| WO | WO 02/096457 | 12/2002 |
| WO | WO 03/009817 | 2/2003 |
| WO | WO 03/039485 | 5/2003 |
| WO | WO 03/068259 | 8/2003 |
| WO | WO 03/072060 A1 | 9/2003 |
| WO | WO 03/072060 A2 | 9/2003 |
| WO | WO 2004/001007 | 12/2003 |
| WO | WO 2004/007520 A2 | 1/2004 |
| WO | WO 2004/016286 | 2/2004 |
| WO | WO 2004/058184 | 7/2004 |
| WO | WO 2004/091658 | 10/2004 |
| WO | WO 2005/019266 | 3/2005 |
| WO | WO 2005/123131 | 12/2005 |
| WO | WO 2006/044908 | 4/2006 |
| WO | WO 2006/081587 | 8/2006 |
| WO | WO 2006/083689 | 8/2006 |
| WO | WO 2006/096461 | 9/2006 |
| WO | WO 2006/096488 | 9/2006 |
| WO | WO 2006/096489 | 9/2006 |
| WO | WO 2006/096490 | 9/2006 |
| WO | WO 2006/096491 | 9/2006 |
| WO | WO 2006/110883 | 10/2006 |
| WO | WO 2007/003936 | 1/2007 |
| WO | WO 2007/019232 | 2/2007 |
| WO | WO 2007/074880 | 7/2007 |
| WO | WO 2007/092772 | 8/2007 |
| WO | WO 2007/147001 | 12/2007 |
| WO | WO 2008/009545 | 1/2008 |
| WO | WO 2008/045563 | 4/2008 |
| WO | WO 2008/071394 | 6/2008 |
| WO | WO 2008/121615 | 10/2008 |
| WO | WO 2008/132439 | 11/2008 |
| WO | WO 2008/157356 | 12/2008 |
| WO | WO 2009/009407 | 1/2009 |
| WO | WO 2009/070642 | 6/2009 |
| WO | WO 2009/077483 | 6/2009 |
| WO | WO 2009/103113 | 8/2009 |
| WO | WO 2009/120684 | 10/2009 |
| WO | WO 2010/000721 | 1/2010 |
| WO | WO 2010/032220 | 3/2010 |
| WO | WO 2010/062896 | 6/2010 |
| WO | WO 2010/072691 | 7/2010 |
| WO | WO 2010/148337 | 12/2010 |
| WO | WO 2011/104381 | 9/2011 |
| WO | WO 2011/109452 | 9/2011 |

OTHER PUBLICATIONS

Carpenter et al.: "Rational design of stable protein formulations: theory and practice"; Pharm Biotechnol. 13:109-33 (2002).

Chang, L. et al. (Sep. 2009, e-pub. Jun. 30, 2009). "Mechanisms of Protein Stabilization in the Solid State," Journal of Pharmaceutical Science 98(9):2886-2908.

Chen, B. et al. (Dec. 2003). "Influence of Histidine on the Stability and Physical Properties of a Fully Human Antibody in Aqueo and Solid Forms", Pharmaceutical Research, vol. 20, No. 12, 1952-1960.

Dalakas; "High-dose intravenous immunoglobulin and serum viscosity: risk of precipitating thromboembolic events"; Neurology 44:223-226 (1994).

Dani, et al.; "High concentration formulation feasibility of human immunoglubulin G for subcutaneous administration"; J Pharm Sci. Jun. 2007;96(6):1504-17.

Daugherty, A., "Formulation and Delivery Issues for Monoclonal Antibody Therapeutics," Advanced Drug Delivery Reviews, 2006, 686-706, vol. 58.

Dráber et al. (1995). "Stability of Monoclonal IgM Antibodies Freeze-Dried in the Presence of Trehalose," Journal of Immunological Methods 181 (1):37-43.

Fahey et al.; "The viscosities of solutions of the proteins of horse serum"; J. Amer. Chem. Soc. 60:3039-3043 (1938).

Galush, et al. "Viscosity behavior of high-concentration protein mixtures"; J Pharm Sci. Mar. 2012;101(3):1012-20.

Garidel, et al. (2009, e-pub. Apr. 16, 2009). "A Thermodynamic Analysis of the Binding Interaction Between Polysorbate 20 and 80 With Human Serum Albumins and Immunoglobulins: A Contribution to Understand Colloidal Protein Stabilisation," Biophysical Chemistry 143:70-78.

Gokarn et al.; "Self-buffering antibody formulations"; J. Pharm. Sci. 97(8):3051-3066 (2008).

Harn, et al.; "Highly concentrated monoclonal antibody solutions: direct analysis of physical structure and thermal stability"; J Pharm Sci. Mar. 2007;96(3):532-46.

Harris et al.; "Commercial manufacturing scale formulation and analytical characterization of therapeutic recombinant antibodies"; Drug Dev. Res. 61:137-154 (2004).

He et al., "Effect of sugar molecules on the viscosity of high concentration monoclonal antibody solutions"; J Pharm Sci. (Nov. 2, 2010). [Epub ahead of print]; Pharm Res. Jul. 2011;28(7):1552-60.

(56) References Cited

OTHER PUBLICATIONS

He, F. et al. (Apr. 2010, e-pub. Sep. 24, 2009). "High Throughput Thermostability Screening of Monoclonal Antibody Formulations," Journal of Phamaceutical Sciences 99(4):1707-1720.
Hess et al.; "The intrinsic viscosity of mixed protein systems, including studies of plasma and serum"; J. Gen. Physiol. 33:511-523 (1950).
Holma, B. et al. (1989). "pH- and Protein-Dependent Buffer Capacity and Viscosity of Respiratory Muc , Their Interrelationships and Influence on Health," The Science of the Total Environment 84:71-82.
Jones, A. (1993). "Analysis of Polypeptides and Proteins." Adv. Drug Delivery Rev. (10)29-90.
Kalapathy et al.; "Alkali-Modified soy proteins: effect of salts and disulfide bond cleavage on adhesion and viscosity"; JAOCS 73(8):1063-1066 (1996).
Kanai et al.; "Reversible Self-Association of a concentrated monoclonal antibody solution mediated by Fab-Fab interaction that impacts solution viscosity"; J Pharm Sci. 97(10):4219-4227 (2008).
Katdare et al.; "Excipient Development for Pharmaceutical Biotechnology and Drug Delivery Systems", from *Excipients for Protein Drugs*, pp. 307-331; Informa Healthcare USA, Inc. (2006) (Gokarn ed.).
Kim et al.; "Diffusivity, viscosity, and cluster formation in protein solutions"; Biotechnol. Bioprocess Eng. 2(1):64-67 (1997).
Kinekawa, et al., (1998). "Effects of Salts on the Properties of Sols and Gels Prepared from Whey Protein Isolate and Process Whey Protein," Journal of Dairy Science 81 (6):1532-1544.
Kochwa et al.; "Aggregation of IgG Globulin in Vivo II. Physicochemcial Properties of the Isolated Protein*"; Biochem. 5(1):277-285 (1966).
Liu J. et al. "Reversible Self-Association Increases the Viscosity of a Concentrated Monoclonal Antibody in Aqueous Solution"; Wiley InterScience DOI 10.1002/jps.20347; Journal of Pharmaceutical Sciences, vol. 94, No. 9, 1928-1940 (2005).
Luo et al., "High-Concentration UF/DF of a Monoclonal Antibody", Bioprocess International, 2006, vol. 4, No. 2, p. 44-48.
Manning et al. (1989). "Stability of Protein Pharmaceuticals" Pharm. Res. 6(11):903-918.
Matheus, et al.; "Liquid high concentration IgG1 antibody formulations by precipitation." J Pharm Sci. Sep. 2009;98(9):3043-57.
Mattern, M. et al. (1999). "Formulation of Proteins in Vacuum-Dried Glasses. II. Process and Storage Stability in Sugar-Free Amino Acid Systems," Pharmaceutical Development and Technology 4(2): 199-208.
Menjivar et al.; "Viscoelastic effects in concentrated protein dispersions"; Rheol. Acta 19:212-219 (1980).
Monkos et al.; "A comparative study on viscosity of human, bovine and pig IgG immunoglobulins in aqueous solutions"; Int. J. Bio. Macromolecules 26:155-159 (1999).
Monkos; "Concentration and temperature dependence of viscosity in lysozyme aqueous solutions"; Biochimica et Biophysica Acta 1339:304-310 (1997).
Monkos; "Viscosity analysis of the temperature dependence of the solution conformation to ovalbumin"; Biophysical Chem. 85:7-16 (2000).
Moore, J., et al.; "Kinetics and Thermodynamics of Dimer Formation and Dissociation for a Recombinant Humanized Monoclonal Antibody to Vascular Endothelial Growth Factor"; Biochemistry 1999, pp. 13960-13967.
Patapoff, et al; (2009). "Polysorbate 20 Prevents the Precipitation of a Monoclonal Antibody During Shear," Pharmaceutical Development and Technology 14(6):659-664.
Pearlman et al. (1991). "Analysis of Protein Drugs," Chapter 6 in *Peptide and Protein Drug Delivery*, Vincent H. L. Lee ed., Marcel Dekker, Inc., pp. 247-301.
Pikal et al. (1991) "The Effects of Formulation Variables on the Stability of Freeze-Dried Human Growth Hormone," Pharmaceutical Research 8:427-436.
Salinas et al.; "Understanding and Modulating Opalescence and Viscosity in a Monoclonal Antibody Formulation", Journal of Pharmaceutical Sciences, 2010, vol. 99, No. 1, pp. 82-93.
Saluja, et al.; "Ultrasonic rheology of a monoclonal antibody (IgG2) solution: implications for physical stability of proteins in high concentration formulations" J Pharm Sci. Dec. 2007;96(12):3181-95.
Saluja et al.; "Nature and consequences of protein-protein interactions in high protein concentration solutions"; Int. J. Pharm. 358:1-15 (2008).
Shire et al.; "Challenges in the development of high protein concentration formulations", Journal of Pharmaceutical Sciences, American Pharmaceutical Association, Washington, US, vol. 93, No. 6, Jun. 1, 2004 (Jun. 1, 2004), pp. 1390-1402, XP009108986, ISSN: 0022-3549, DOI: 10.1002/jps.20079 p. 1396, right-hand column.
Siegel, "Tonicity, Osmoticity, Osmolality and Osmolarity" Ch. 79 in Remington's Pharmaceutical Sciences, 18th Ed., pp. 1481-1498 (Gennaro ed, Mack Publishing Co., 1990).
Szencizi, et al.; "The effect of solvent environment on the conformation and stability of human polyclonal IgG in solution"; Biologicals. Mar. 2006; 34(1):5-14.
Tanford et al.,; "The Viscosity of Aqueous Solutions of Bovine Serum Albumin Between *p*H 4.3 and10.5[1]" J. Phys. Chem. 60:225-231 (1956).
Tian, F. et al. (2003). "Spectroscopic Evaluation of the Stabilization of Humanized Monoclonal Antibodies in Amino Acid Formulations," International Journal of Pharmaceutics 335:20-31.
Wang et al. (Jan. 2007), "Antibody Structure, Instability, and Formulation," Journal of Pharmaceutical Sciences 96(1):1-26.
Wang et al., BioPharm. Int. "Opalescence of an IgG1 Monoclonal Antibody Formulation . . . " pp. 36-47 (2009).
Wang; "Instability, stabilization, and formulation of liquid protein pharmaceuticals"; Int. J. Pharm. 185:129-188 (1999).
Yadav, et al.; "Factors affecting the viscosity in high concentration solutions of different monoclonal antibodies." J Pharm Sci. Dec. 2010;99(12):4812-29.
Yadav, et al.; "Viscosity analysis of high concentration bovine serum albumin aqueous solutions." Pharm Res. Aug. 2011;28(8):1973-83.
Yadav, et al.; "Viscosity behavior of high-concentration monoclonal antibody solutions: correlation with interaction parameter and electroviscous effects"; J Pharm Sci. Mar. 2012;101(3):998-1011.
Yadav, et al.; "Specific interactions in high concentration antibody solutions resulting in high viscosity."; J Pharm Sci. Mar. 2010;99(3):1152-68.
Yousef, M.A. et al. (1998). "Free-Solvent Model of Osmotic Pressure Revisited: Application to Concentrated IgG Solution under Physiological Conditions." Journal of Colloid and Interface Science 197:p. 108-118.

* cited by examiner

ANTIBODY AND PROTEIN FORMULATIONS

The present application is a continuation-in-part application of U.S. application Ser. No. 13/601,598, entitled "HIGH CONCENTRATION ANTIBODY AND PROTEIN FORMULATIONS" issued as U.S. Pat. No. 8,613,919 and filed Aug. 31, 2012, and the entire disclosure is hereby expressly incorporated herein by reference.

BACKGROUND

The present disclosure relates generally to antibody and other protein formulations that are isosmotic and of low viscosity, including formulations that are useful for injection and general administration.

Hemophilia patients have bleeding disorders that result in delayed blood clotting after an injury or surgery. Prolonged bleeding is caused by a genetic deficiency in one or more blood clotting factor. Two common types of hemophilia are known—hemophilia A and hemophilia B. Hemophilia A is caused by a deficiency in factor VIII whereas hemophilia B is caused by a deficiency in factor IX. About 75-80% of total hemophilia patients have hemophilia A.

Tissue factor pathway inhibitor (TFPI) is a human inhibitor of the extrinsic pathway of blood coagulation and functions in anticoagulation. Antibodies that are directed against TFPI, including anti-TFPI monoclonal antibodies (aTFPI mAb), are being developed in an effort to block TFPI function. One such aTFPI mAb is a human IgG2 anti-TFPI mAb. that is being developed for the treatment of hemophilia A and B patients.

Antibody and other proteins may be administrated to patients via intravenous, intramuscular, and/or subcutaneous injection. To ensure patient compliance, it is desirable that subcutaneous injection dosage forms be isotonic and include small injection volumes (<2.0 ml per injection site). To reduce injection volume, proteins are often administered within the range of 1 mg/ml to 150 mg/ml.

While both liquid and lyophilized dosage forms are used for currently marketed antibody and other protein-based drug products, lyophilized forms are more frequently used for protein and antibody drug products having high protein concentrations.

A protein and antibody dosage form may present many challenges in formulation development, especially for liquid formulation. For formulations in which the protein concentration is near its apparent solubility limit, phase separation can occur through precipitation, gelation, and/or crystallization. At high protein concentration, the stability of an antibody or other protein can become problematic due to the formation of soluble and insoluble protein-protein aggregates. Highly concentrated protein formulations are frequently highly viscous, which presents difficulties for processing, such as ultrafiltration and sterile filtration, and for injection of the dosage solution. And at protein concentrations that are desirable for formulations intended for intramuscular or subcutaneous administration, high concentrations of stabilizers, such as sucrose and sodium chloride, are required to achieve long-term protein stability. The resulting hypertonic solutions often cause injection pain due to tissue damage. Therefore, it is critical to balance the amount of stabilizers for stability and osmolality of the high protein concentration formulation.

For these reasons, there is a need in the art for antibody and other protein-based therapeutic formulations in liquid form that exhibit high protein concentrations without the problem of significantly increased protein aggregation, osmolality, or viscosity and/or decreased protein stability. It is, therefore, desirable that antibody and other protein-based formulations contain limited amounts of excipients and small volumes for ease of therapeutic administration or delivery. It is further desirable that antibody and other protein-based therapeutic formulations be amenable to lyophilization to enhance protein stability under prolonged storage conditions.

SUMMARY

The present disclosure provides liquid and lyophilized antibody and protein-based formulations that are substantially isotonic and low viscosity and that contain substantially no inorganic salt. The antibody and other protein formulations presented herein contain from about 0 mM to about 30 mM histidine; from about 50 ppm to about 200 ppm of a non-ionic surfactant such as, for example, polysorbate (Tween®) 80 or polysorbate (Tween®) 20; from about 88 mM to about 292 mM of a sugar or sugar alcohol such as, for example, mannitol, dextrose, glucose, trehalose, and/or sucrose; from about 0 mM to about 50 mM arginine; from about 0 mM to about 50 mM lysine; from about 0 mM to about 133 mM glycine or alanine; from about 0 mM to about 10 mM methionine; and from about 1 mg/ml to about 150 mg/ml of a protein at a pH from about pH 4.0 to about pH 6.0. The formulations disclosed herein exhibit a viscosity ranging from about 1 mPa-S to about 20 mPa-S at 22° C., or from about 1 mPa-S to about 15 mPa-S at 22° C., or from about 1 mPa-S to about 10 mPa-S at 22° C. or from about 1 mPa-S to about 8 mPa-S at 22° C. or from about 1 mPa-S to about 6 mPa-S at 22° C. and osmolality ranging from about 240 to about 380 mmol/kg.

Within further aspects, the present disclosure provides methods for the treatment of a disorder in a patient, comprising the administration to the patient of a therapeutically effective amount of one or more formulations described herein. For example, provided are methods for the treatment of a disorder in a patient, comprising the administration to the patient of a therapeutically effective amount of an antibody or other protein formulation as described in greater detail herein.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF VARIOUS EMBODIMENTS

Figure 1:
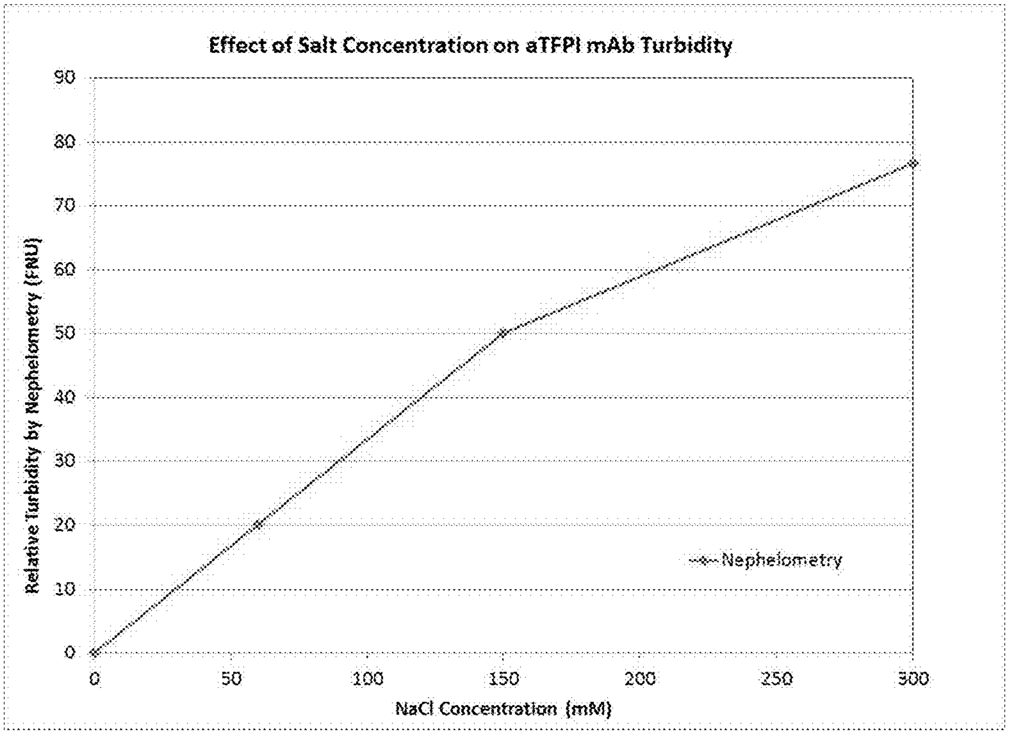
FIG. 1 is a graph showing the effect of sodium chloride (NaCl) concentration on the turbidity of 20 mg/ml anti-TFPI mAb formulations at pH 5.5.

As described above, the present disclosure provides antibody and other protein formulations that stabilize the antibody or other protein in liquid form or lyophilized form at intended storage conditions. The formulations described herein include one or more pharmaceutically acceptable excipients or stabilizers, and are contained in buffered media at a suitable pH and are substantially isosmotic with physiological fluids. For systemic administration, injection is one route of administration, including intramuscular, intravenous, intraperitoneal, and subcutaneous injection.

Because of their low viscosity, the presently disclosed protein formulations can be conveniently processed via, for example, ultrafiltration and sterile filtration and can be administered to a patient via injection, including subcutaneous injection. Moreover, because they are substantially isosmotic, the presently disclosed antibody and protein formulations reduce tissue damage or other adverse physiologic effects and thereby achieving favorable patient tolerance and increased patient compliance.

The formulations described herein are characterized by the substantial absence of added salt, which provides the flexibility for increasing the concentrations of other stabilizers, such as sucrose, while maintaining the osmolality of the formulation for improved in vivo tolerability and, consequently, increased patient compliance. Moreover, the low viscosity of the presently described formulations permits convenient processing, including but not limited to ultrafiltration and sterile filtration, and injection of the drug product solution through the needle.

As used herein, the term "viscosity" refers to the resistance of a liquid formulation to flow, such as when injected through a syringe needle during administration to a patient. Viscosity measurements can be done by a cone and plate technique with a Peltier element set at a defined temperature, such as 22° C. as described herein. Typically, a well-defined shear stress gradient is applied to the liquid formulation and the resulting shear rate is measured. The viscosity is the ratio of the shear stress to the shear rate. As used herein, viscosity is expressed in units of mPa-S at 22° C. wherein 1 mPa-S=1 cP. The low viscosity, substantially isosmotic formulations disclosed herein are typically characterized by having a viscosity ranging from about 1 mPa-S to about 20 mPa-S at 22° C., or from about 1 mPa-S to about 15 mPa-S at 22° C., or from about 1 mPa-S to about 10 mPa-S at 22° C. or from about 1 mPa-S to about 8 mPa-S at 22° C. or from about 1 mPa-S to about 6 mPa-S at 22° C.

As used herein, the term "osmolality" refers to a measure of solute concentration, defined as the number of mmole of solute per kg of solution. A desired level of osmolality can be achieved by the addition of one or more stabilizer such as a sugar or sugar alcohol including, but not limited to, mannitol, dextrose, glucose, trehalose, and/or sucrose. Additional stabilizers that are suitable for providing osmolality are described in references such as the handbook of Pharmaceutical Excipients (Fourth Edition, Royal Pharmaceutical Society of Great Britain, Science & Practice Publishers) or Remingtons: The Science and Practice of Pharmacy (Nineteenth Edition, Mack Publishing Company).

As used herein, the term "about" refers to +/−10% of the unit value provided. As used herein, the term "substantially" refers to the qualitative condition of exhibiting a total or approximate degree of a characteristic or property of interest. One of ordinary skill in the biological arts will understand that biological and chemical phenomena rarely, if ever, achieve or avoid an absolute result. The term substantially is therefore used herein to capture the potential lack of completeness inherent in many biological and chemical phenomena. As used herein, the terms "isosmotic" and "isotonic" are used interchangeably with the terms "substantially isosmotic," and "substantially isotonic" and refer to formulations characterized by having an osmotic pressure that is the same as or at least substantially equivalent to the osmotic pressure of another solution, which is achieved by formulations wherein the total concentration of solutes, including both permeable and impermeable solutes, in the formulation are the same as or at least substantially equivalent to the total number of solutes in another solution. Thus, while it will be appreciated by those of skill in the art that "isosmotic" and "isotonic" formulations that are used for in vivo administration generally have an osmolality ranging from about 270 mmol/kg to about 310 mmol/kg, in the context of the low viscosity formulations of the present disclosure, the terms "isosmotic," "isotonic," "substantially isosmotic," and "substantially isotonic" are used interchangeably to refer to formulations having an osmolality ranging from about 240 mmol/kg to about 380 mmol/kg, or from about 270 mmol/kg to about 370 mmol/kg, or from about 300 mmol/kg to about 330 mmol/kg.

The presently disclosed low viscosity, substantially isosmotic antibody and other protein formulations contain from about 0 mM to about 30 mM histidine; from about 50 ppm to about 200 ppm of a non-ionic surfactant such as, for example, polysorbate (Tween®) 80 or polysorbate (Tween®) 20; from about 88 mM to about 292 mM of a sugar or sugar alcohol such as, for example, mannitol, dextrose, glucose, trehalose, and/or sucrose; from about 0 mM to about 50 mM arginine; from about 0 mM to about 50 mM lysine; from about 0 mM to about 133 mM glycine or alanine; from about 0 mM to about 10 mM methionine; and from about 1 mg/ml to about 150 mg/ml of a protein at a pH from about pH 4 to about pH 6. The formulations disclosed herein exhibit a viscosity ranging viscosity ranging from about 1 mPa-S to about 20 mPa-S at 22° C., or from about 1 mPa-S to about 15 mPa-S at 22° C., or from about 1 mPa-S to about 10 mPa-S at 22° C. or from about 1 mPa-S to about 8 mPa-S at 22° C. or from about 1 mPa-S to about 6 mPa-S at 22° C. and osmolality ranging from about 240 to about 380 mmol/kg.

In these formulations, histidine—is a buffer agent, that can be used to maintain the formulation pH from about pH 4 to about pH 6.0, or about pH 5 to about pH 6, such as about pH 5, about pH 5.5, or about pH 6. Sugar or sugar alcohols, such as mannitol, dextrose, glucose, trehalose, and/or sucrose, are used separately or in combination, both as cryo-protectants and a stabilizer the antibody in liquid formulations as well as during and after lyophilization. Non-ionic surfactants such as polysorbates, including polysorbate 20 and polysorbate 80; polyoxamers, including poloxamer 184 and 188; Pluronic® polyols; and other ethylene/polypropylene block polymers, stabilize the antibody during processing and storage by reducing interfacial interaction and prevent protein from adsorption. Arginine is a protein solubilizer and also a stabilizer that reduces antibody and other protein aggregation, such as aTFPI mAb aggregation, and glycation. Methionine is an antioxidant that prevents antibody oxidation during processing and storage.

Sugars and inorganic salts are commonly used as protein stabilizers; however, both sugars and inorganic salts are also effective tonicity agents. If a formulation requires a high concentration of one or more sugars to stabilize a protein, the inorganic salt concentration should be zero or kept very low in order to maintain the formulation's osmolality such that injection pain is reduced upon administration. Quite surprisingly, it was found that sodium chloride increased the turbidity of antibody formulations. Consequently, inorganic salts are substantially excluded from addition to the formulations described herein. These non-salt formulations maintain the osmolality of the antibody and other protein formulations with increased stability, and reduced phase change, such as precipitation or aggregation.

As used herein, the term "salt" refers to inorganic salts, which include but not limited to sodium chloride (NaCl), sodium sulfate ($Na_2SO_4$), sodium thiocyanate (NaSCN), magnesium chloride (MgCl), magnesium sulfate ($MgSO_4$), ammonium thiocyanate ($NH_4SCN$), ammonium sulfate ($(NH_4)_2SO_4$), ammonium chloride ($NH_4Cl$), calcium chloride ($CaCl_2$), calcium sulfate ($CaSO_4$), zinc chloride ($ZnCl_2$) and the like, or combinations thereof. The antibody and other protein formulations disclosed herein are characterized by a substantial absence of added salt and are, therefore, referred to herein as salt-free antibody and/or protein formulations. It will be understood by those of skill in the art that the presence of inorganic salts within the presently disclosed formulations that are introduced by pH adjustment are not considered to be added salts and such inorganic salts, if present in a formulation according to the present disclosure, should not exceed a concentration of about 2 mM.

As used herein, the term "surfactant" includes non-ionic surfactants including, without limitation, polysorbates, such as polysorbate 20 or 80, and the polyoxamers, such as poloxamer 184 or 188, Pluronic® polyols, and other ethylene/polypropylene block polymers. Amounts of surfactants effective to provide stable antibody and other protein formulations are usually in the range of 50 ppm to 200 ppm. The use of non-ionic surfactants permits the formulations to be exposed to shear and surface stresses without causing denaturation of the antibody or other protein, and also reduce the adsorption on the surfaces during processing and storage. The formulations disclosed herein include, without limitation, formulations having one or more non-ionic surfactant(s) including, for example, one or more polysorbate(s), such as polysorbate 20 or 80; one or more polyoxamers, such as poloxamer 184 or 188; one or more Pluronic® polyol(s); and/or one or more ethylene/polypropylene block polymer(s). Exemplified herein are formulations having a polysorbate, such as polysorbate 20 (Tween® 20) or polysorbate 80 (Tween® 80).

As used herein, the term "protein" refers to amino acid polymers that contain at least five constituent amino acids that are covalently joined by peptide bonds. The constituent amino acids can be from the group of amino acids that are encoded by the genetic code, which include: alanine, valine, leucine, isoleucine, methionine, phenylalanine, tyrosine, tryptophan, serine, threonine, asparagine, glutamine, cysteine, glycine, proline, arginine, histidine, lysine, aspartic acid, and glutamic acid. As used herein, the term "protein" is synonymous with the related terms "peptide" and "polypeptide".

As used herein, the term "antibody" refers to a class of proteins that are generally known as immunoglobulins Antibodies include full-length monoclonal antibodies (mAb), such as $IgG_2$ monoclonal antibodies, which include immunoglobulin Fc regions. The term antibody also includes bispecific antibodies, diabodies, single-chain molecules, and antibody fragments such as Fab, $F(ab')_2$, and Fv.

As used herein, the term "anti-TFPI antibody" refers to an antibody having binding specificity against the human TFPI protein as well as fragments and variants of the human TFPI protein. Anti-TFPI antibodies presented herein can be IgG2 antibodies and include anti-TFPI IgG2 monoclonal antibodies, such as chimeric, humanized, and fully-human anti-TFPI IgG2 monoclonal antibodies. Anti-TFPI antibodies are exemplified in the present disclosure by human anti-TFPI IgG2 monoclonal antibodies having a light chain comprising the sequence presented herein as SEQ ID NO: 1 and/or a heavy chain presented herein as SEQ ID NO: 2. Other anti-TFPI monoclonal antibodies, including full-length antibodies and antigen binding fragments and variants thereof, that are also suitable for use in the formulations disclosed herein are presented in PCT Patent Publication NOs. WO 2011/109452 and WO 2010/017196, both of which are incorporated by reference herein in their entirety.

"Monoclonal antibodies" are characterized by having specificity for a single antigenic determinant. Monoclonal antibodies can, for example, be made by the hybridoma method described by Kohler and Milstein, *Nature* 256:495 (1975) or by recombinant DNA methods such as those described in U.S. Pat. No. 4,816,567. Monoclonal antibodies can also be isolated from phage display libraries using the techniques such as those described in Clackson et al., *Nature* 352:624-628 (1991) and Marks et al., *J. Mol. Biol.* 222:581-597 (1991).

Monoclonal antibodies include "chimeric monoclonal antibodies" wherein a portion of a heavy and/or light chain includes sequences from antibodies derived from one species, while the remainder of the antibody, including the Fc region, includes sequences from antibodies derived from a second species, typically the second species is human. See, e.g., U.S. Pat. No. 4,816,567 and Morrison et al., *Proc. Natl. Acad. Sci. USA* 81:6851-6855 (1984).

Monoclonal antibodies also include "humanized monoclonal antibodies" wherein one or more complementarity determining region (CDR) from a heavy and/or light chain sequence from antibodies derived from one species replace one or more CDR from a heavy and/or light chain sequence from antibodies derived from a second species, typically the second species is human. The process of "humanization" is usually applied to monoclonal antibodies developed for administration to humans. See, e.g., Riechmann et al., *Nature* 332(6162):323-27 (1988) and Queen et al., *Proc. Natl. Acad. Sci. USA* 86(24):10029-33 (1989).

Monoclonal antibodies also include "fully-human monoclonal antibodies" wherein the entire heavy and light chain sequences are derived from human antibody sequences. Fully-human monoclonal antibodies can be generated by phage display technologies and can be isolated from mice that have been genetically engineered to express the human antibody repertoire. See, e.g., McCafferty et al., *Nature* 348(6301):552-554 (1990), Marks et al., *J. Mol. Biol.* 222 (3):581-597 (1991), and Carmen and Jermutus, *Brief Funct. Genomic Proteomic* 1(2):189-203 (2002).

As used herein, the term "Pharmaceutically effective amount" of an antibody or other protein formulation refers to an amount of the formulation that provides therapeutic effect in an administration regimen. The antibody and protein formulations disclosed herein typically include an antibody or other protein at a concentration ranging from about 1 mg/ml to about 150 mg/ml, or from about 1 mg/ml to about 100 mg/ml, or from about 1 mg/ml to about 50 mg/ml, or from about 1 mg/ml to about 20 mg/ml, or from about 1 mg/ml to about 10 mg/ml, or from about 10 mg/ml to about 20 mg/ml, or from about 20 mg/ml to about 150 mg/ml, or from about 50 mg/ml to about 150 mg/ml, or from about 60 mg/ml to about 150 mg/ml, or from about 70 mg/ml to about 150 mg/ml, or from about 80 mg/ml to about 150 mg/ml, or from about 90 mg/ml to about 150 mg/ml, or from about 100 mg/ml to about 150 mg/ml, or from about 120 mg/ml to about 150 mg/ml, or from about 140 mg/ml to about 150 mg/ml, Within some aspects the concentration of protein or antibody within these formulations is about 150 mg/ml. When administered subcutaneously, such formulations are typically administered in a volume of less than about 2.0 ml, or about 1.5 ml, or about 1 ml, or about 0.5 ml per injection site.

Within certain aspects, the antibody or other protein formulation contains about 30 mM histidine, about 100 ppm Tween 80, about 292 mM sucrose, about 20 mg/ml antibody or other protein at a pH ranging from about pH 5.0 to about pH 6.0. Within related aspects, the antibody and other protein formulation also contains from about 30 mM to about 50 mM arginine.

Within other aspects, the antibody or other protein formulation contains about 10 mM histidine, about 75 ppm Tween 80, about 234 mM sucrose, about 50 mg/ml antibody or other protein at a pH ranging from about pH 5.0 to about pH 6.0. Within related aspects, the antibody and other protein formulation also contains from about 30 mM to about 50 mM arginine.

Within other aspects, the antibody or other protein formulation contains about 10 mM histidine, about 75 ppm Tween 80, about 234 mM sucrose, about 100 mg/ml antibody or other protein at a pH ranging from about pH 5.0 to about pH 6.0. Within related aspects, the antibody and other protein formulation also contains from about 30 mM to about 50 mM arginine.

Within other aspects, the antibody or other protein formulation contains about 10 mM histidine, about 75 ppm Tween 80, about 88 mM sucrose, about 133 mM glycine, about 100 mg/ml antibody or other protein at a pH ranging from about pH 5.0 to about pH 6.0. Within related aspects, the antibody and other protein formulation also contains from about 30 mM to about 50 mM arginine.

Within other aspects, the antibody or other protein formulation contains about 10 mM histidine, about 75 ppm Tween 20, about 88 mM sucrose, about 133 mM glycine, about 100 mg/ml antibody or other protein at a pH ranging from about pH 5.0 to about pH 6.0. Within related aspects, the antibody and other protein formulation also contains from about 30 mM to about 50 mM arginine.

Within other aspects, the antibody or other protein formulation contains about 10 mM histidine, about 200 ppm Tween 20, about 88 mM sucrose, about 133 mM glycine, about 100 mg/ml antibody or other protein at a pH ranging from about pH 5.0 to about pH 6.0. Within related aspects, the antibody and other protein formulation also contains from about 30 mM to about 50 mM arginine.

Within other aspects, the antibody or other protein formulation contains about 10 mM histidine, about 75 ppm Tween 80, about 88 mM sucrose, about 100 mg/ml antibody or other protein at a pH ranging from about pH 5.0 to about pH 6.0. Within related aspects, the antibody and other protein formulation also contains from about 10 mM to about 50 mM arginine.

Within other aspects, the antibody or other protein formulation contains about 10 mM histidine, about 75 ppm Tween 80, about 88 mM sucrose, about 133 mM glycine, about 10 mM arginine, about 100 mg/ml antibody or other protein at a pH ranging from about pH 5.0 to about pH 6.0. Within related aspects, the antibody and other protein formulation also contains from about 0 mM to about 10 mM methionine.

Within other aspects, the antibody or other protein formulation contains about 10 mM histidine, about 75 ppm Tween 80, about 88 mM sucrose, about 133 mM glycine, about 30 mM lysine, about 100 mg/ml antibody or other protein at a pH ranging from about pH 5.0 to about pH 6.0.

Within other aspects, the antibody or other protein formulation contains about 10 mM histidine, about 75 ppm about Tween 80, about 234 mM sucrose, about 30 mM arginine, about 100 mg/ml antibody or other protein at a pH ranging from about pH 5.0 to about pH 6.0. Within related aspects, the antibody and other protein formulation also contains from about 0 mM to 10 mM methionine.

Exemplified herein are antibody formulations wherein the antibodies include IgG2 antibodies, such as anti-tissue factor pathway inhibitor antibodies (aTFPI Abs), including the human IgG2 monoclonal antibody having a light chain comprising the sequence of SEQ ID NO: 1 and a heavy chain comprising the sequence of SEQ ID NO: 2.

Thus, the present disclosure provides anti-TFPI mAb formulations, including anti-TFPI $IgG_2$ mAb formulations, wherein the anit-TFPI mAb is soluble at high protein concentrations. Typically, the anti-TFPI mAb in the formulations disclosed herein remain soluble at concentrations of between about 1 mg/ml and about 150 mg/ml and remain stable under isosmotic storage conditions and exhibit reduced viscosity as compared to currently available antibody formulations.

The anti-TFPI antibody having a light chain comprising the sequence of SEQ ID NO: 1 and a heavy chain comprising the sequence of SEQ ID NO: 2 is an $IgG_2$ antibody that blocks tissue factor pathway inhibitor (TFPI). Since TFPI down-regulates extrinsic coagulation, anti-TFPI antibodies can promote extrinsic pathway-driven coagulation by blocking TFPI, thereby bypassing FVIII or FIX deficiencies in the intrinsic pathway for hemophilia treatment. The salt free anti-TFPI antibody formulations presented herein can be administrated to the patients via subcutaneous injection or other injection routes.

As part of the present disclosure, it was found that solubility and stability of anti-TFPI antibodies was affected by excipients. The solubility of anti-TFPI antibody increases with the decrease of NaCl concentrations. In the absence of NaCl, the solubility of anti-TFPI antibody is higher than formulations that include NaCl. In addition, it was found that positively changed amino acids, such as arginine and lysine, could improve the stability anti-TFPI antibody and that pH greatly affected the anti-TFPI antibody solubility. The turbidity of the antibody solution increased with increases in pH; however, the precipitation was reversible when pH was decreased. The optimal pH for stabilizing the anti-TFPI antibodies presented herein ranges from about pH 4 to about pH 6 or from about pH 5 to about pH 6, such as about pH 5, about pH 5.5, or about pH 6.

Exemplified herein are formulations, as recited above, wherein the antibody is an anti-TFPI antibody (aTFPI Ab). In at least one aspect, the anti-TFPI antibody is a human IgG2 monoclonal antibody. For example, the human anti-TFP1 IgG2 monoclonal antibody includes the antibody that contains a light chain having the amino acid sequence presented in SEQ ID NO: 1 and a heavy chain having the amino acid sequence presented in SEQ ID NO: 2.

Heavy and Light Chain Sequences of an Exemplary Human Anti-TFPI IgG2 Monoclonal Antibody

| Sequence Identifier | Amino Acid Sequence ($NH_3$-COOH) |
|---|---|
| SEQ ID NO: 1 | SYELTQPPSV SVSPGQTARI TCSGDNLPKY YAHWYQQKPG QAPVVVIFYD VNRPSGIPER FSGSNSGNTA TLTISGTQAM DEADYYCQAW WSSTPVFGGG TKLTVLGQPK AAPSVTLFPP SSEELQANKA TLVCLISDFY PGAVTVAWKA DSSPVKAGVE TTTPSKQSNN KYAASSYLSL TPEQWKSHRS YSCQVTHEGS TVEKTVAPTE CS |
| SEQ ID NO: 2 | EVQLVESGGG LVQPGGSLRL SCAASGFTFS SYGMDWVRQA PGKGLEWVSS IRGSRGSTYY |

-continued

Heavy and Light Chain Sequences of an Exemplary Human Anti-TFPI IgG2 Monoclonal Antibody

| Sequence Identifier | Amino Acid Sequence ($NH_3$-COOH) |
|---|---|
| | ADSVKGRFTI SRDNSKNTLY LQMNSLRAED TAVYYCARLY RYWFDYWGQG TLVTVSSAST KGPSVFPLAP CSRSTSESTA ALGCLVKDYF PEPVTVSWNS GALTSGVHTF PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ FNWYVDGVEV HNAKTKPREE QFNSTFRVVS VLTVVHQDWL NGKEYKCKVS NKGLPAPIEK TISKTKGQPR EPQVYTLPPS REEMTKNQVS LTCLVKGFYP SDIAVEWESN GQPENNYKTT PPMLDSDGSF FLYSKLTVDK SRWQQGNVFS CSVMHEALHN HYTQKSLSLS PG |

The present disclosure also provides methods for the treatment of a disorder in a patient, comprising the administration to the patient of a therapeutically effective amount of one or more formulations described herein. For example, provided are methods for the treatment of a disorder in a patient, comprising the administration to the patient of a therapeutically effective amount of an antibody or other protein formulation that contains from about 0 mM to about 30 mM histidine and, from about 50 ppm to about 200 ppm polysorbate (Tween®) 80 or polysorbate (Tween®) 20, from about 88 mM to about 292 mM sucrose, from about 0 mM to about 50 mM arginine, from about 0 mM to about 50 mM lysine, from about 0 mM to about 133 mM glycine or alanine, from about 0 mM to about 10 mM methionine, and from about 1 mg/ml to about 150 mg/ml of a protein at a pH ranging from about pH 4.0 to about pH 6.0. Within at least one aspect of these methods, the antibody or other protein formulation can be administered intravenously. Within other aspects of these methods, the antibody or other protein formulation can be administered subcutaneously. Within other aspects of these methods, the antibody or other protein formulation can be administered intramuscularly.

Within related aspects, the present disclosure provides methods for the treatment of hemophilia A or hemophilia B in a patient, comprising the administration to the patient of a therapeutically effective amount of an anti-TFPI antibody formulation that contains from about 0 mM to about 30 mM histidine and, from about 50 ppm to about 200 ppm polysorbate (Tween®) 80 or polysorbate (Tween®) 20, from about 88 mM to about 292 mM sucrose, from about 0 mM to about 50 mM arginine, from about 0 mM to about 50 mM lysine, from about 0% (0 mM) to about 1% (133 mM) glycine, from about 0 mM to about 10 mM methionine, and from about 1 mg/ml to about 150 mg/ml of a protein at a pH ranging from about pH 4.0 to about pH 6.0. Within at least one aspect of these methods, the anti-TFPI antibody formulation can be administered intravenously. Within other aspects of these methods, the anti-TFPI antibody formulation can be administered subcutaneously. Within other aspects of these methods, the antibody or other protein formulation can be administered intramuscularly.

According to certain aspects of these methods for the treatment of hemophilia A or hemophilia B in a patient, the anti-TFPI antibody is a human anti-TFP1 IgG2 monoclonal antibody such as, for example, the human anti-TFPI IgG2 monoclonal antibody that contains a light chain having the amino acid sequence presented in SEQ ID NO: 1 and a heavy chain having the amino acid sequence presented in SEQ ID NO: 2.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

Aspects of the present disclosure may be further understood in light of the following examples, which should not be construed as limiting the scope of the present teachings in any way.

EXAMPLES

Example 1

Effect of NaCl Concentration and pH on the Turbidity of Antibody Solutions

This Example discloses the effect of salt (NaCl) concentration and pH on the turbidity of solutions containing an anti-TFPI human monoclonal antibody having a light chain with the amino acid sequence presented in SEQ ID NO: 1 and a heavy chain with the amino acid sequence presented in SEQ ID NO: 2.

The turbidity of solutions was measured by Nephelometry to quickly evaluate the effects of salt concentrations and pH on aTFPI Ab solutions. The formulation of anti-TFPI antibody used in this Example contained 10 mM acetate buffer, 88 mM sucrose, and 200 ppm Tween 80. NaCl concentrations were varied from 0 mM to 300 mM. The results of NaCl-dependent turbidity measurements for anti-TFPI formulations at pH 5.5 are presented in FIG. 1. These data demonstrated that the turbidity of the anti-TFPI mAb formulations increased significantly with increasing concentration of NaCl. Increasing salt concentration from 0 to 300 mM resulted in an increase of 72 FNU in turbidity value by Nephelometry, which could be attributed to precipitation, aggregation or insolubilization of aTFPI Ab in solution. As the result of this finding, solutions without sodium chloride were recommended for the presently disclosed anti-TFPI antibody formulations.

Without being bound by theory, it is believed that the increased turbidity of the anti-TFPI mAb formulations with increasing NaCl concentration resulted from the neutralization of positive charges on the anti-TFPI mAb arginine side-chains. The phase behavior of aTFPI mAb at different pH with the impact of monovalent salt (NaCl) explains why the stable, soluble, non-salt, and substantial isosmolality aTFPI mAb formulations could be achieved.

The presently disclosed aTFPI mAb molecule has 116 amino acids (42 arginines and 74 lysines) having side-chain carrying positive charges at the pH below PI. This anti-TFPI antibody has a PI at ~7.9. At a pH below the PI, such as pH 4-6, this anti-TFPI antibody has net positive charges. The repulsion of the positive charges on this anti-TFPI antibody surface likely prevents protein-protein association between individual molecules and, thereby, significantly increases solubility. It is hypothesized that the anion ($Cl^-$) of salt binds to the guanidinium group on arginine side-chains on the anti-TFPI antibody surface to neutralize the positive charges, which enhances protein-protein interactions and, hence, causes lower solubility and solution turbidity. By shifting the pH to 4-6, the non-salt formulations that are described herein were developed to achieve increased antibody solubility and stability (see, FIG. 1). In absence of salt, the concentration of other stabilizers, such as sucrose, can be increased to >150 mM and <300 mM without compromising osmolality.

Figure 2:
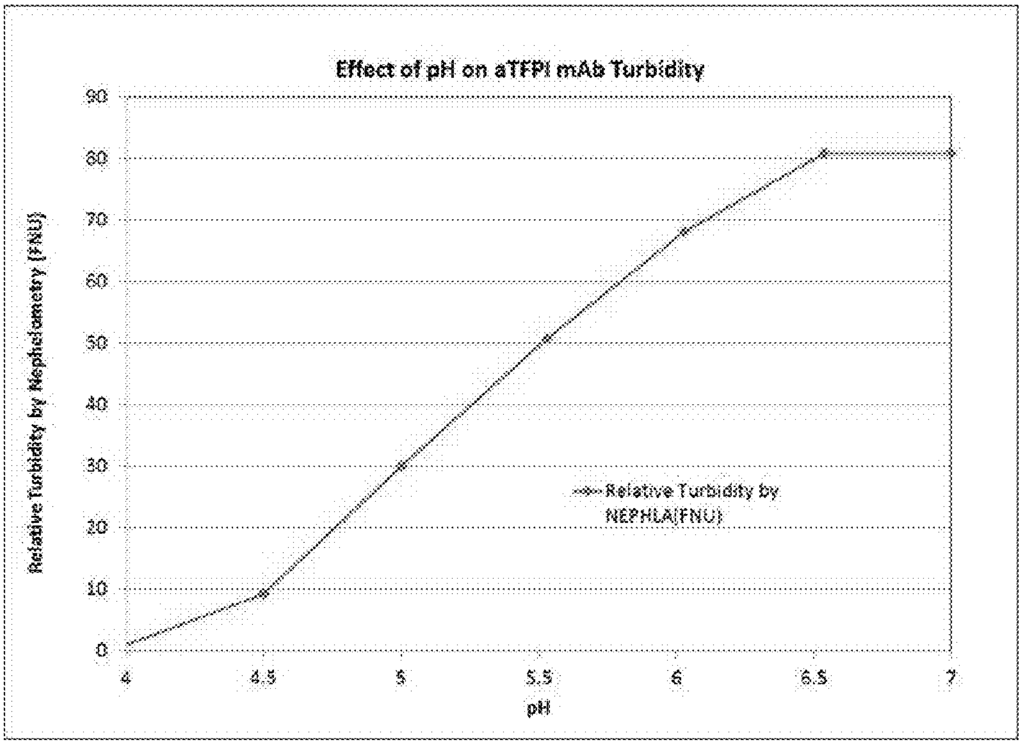
FIG. 2 is a graph showing the effect of pH on the turbidity of an anti-TFPI mAb drug substance.

The effect of pH on the turbidity of anti-TFPI antibodies was also studied. As shown in FIG. 2, pH can also greatly affect the turbidity of aTFPI Ab solution. When pH was increased from 4 to 6.5, the turbidity of aTFPI Ab solution increased by 81 FNU. Further increasing pH to 7, the turbidity of solution was out of the range for accurate measurement. However, the formed precipitates in the solution were reversible when pH was decreased. This result could be attributed to the surface charge neutralization when pH was increased to the value close to the PI of aTFPI Ab, since the PI value of aTFPI Ab is approximately 7.9. According to this study, lower pH was preferred for aTFPI Ab formulations. However, low pH could cause tissue irritation during injection. Therefore, a neutral pH was preferred from patient compliance point of view. Balancing these two factors, the optimum pH of aTFPI Ab formulations is between pH 5 and pH 6.

Example 2

Anti-TFPI Antibody Formulations

Based upon the unexpected findings presented in Example 1, substantially isosmotic anti-TFPI Ab formulations were prepared without NaCl. These formulations typically employed high sucrose concentrations to help stabilize the anti-TFPI Ab.

Frozen anti-TFPI antibody was thawed and reformulated by dialysis according to formulations presented in Table 1. The formulations were prepared and were filtered with a 0.22 μm filter and filled in glass tubing vials and stoppered with rubber stoppers.

It was also found that in the absence of NaCl, and in the presence of sucrose 88 mM to 292 mM and polysorbate 80 or polysorbate 20 (50-200 ppm), the positive charged amino acids, such as arginine (10-50 mM), can effectively inhibit aTFPI Ab from glycation.

TABLE 1

Anti-TFPI Antibody Formulations

| Formulation Designation | Formulation Composition |
|---|---|
| PH5.0 | 20 mg/ml aTFPI mAb<br>30 mM histidine<br>292 mM sucrose<br>100 ppm Tween 80<br>pH 5.0 |
| PH5.5 | 20 mg/ml aTFPI mAb<br>30 mM histidine<br>292 mM sucrose<br>100 ppm Tween 80<br>pH 5.5 |
| PH6.0 | 20 mg/ml aTFPI mAb<br>30 mM histidine<br>292 mM sucrose<br>100 ppm Tween 80<br>pH 6.0 |
| 6ARG | 20 mg/ml aTFPI mAb<br>30 mM histidine<br>292 mM sucrose<br>100 ppm Tween 80<br>50 mM arginine<br>pH 6.0 |
| PH5.5LC | 50 mg/ml aTFPI Ab<br>10 mM histidine<br>234 mM sucrose<br>75 ppm Tween 80<br>pH 5.5 |
| PH5.5LCARG | 50 mg/ml aTFPI Ab<br>10 mM histidine<br>234 mM sucrose<br>75 ppm Tween 80<br>30 mM arginine<br>pH 5.5 |
| PH5.5HCARG | 100 mg/ml aTFPI Ab<br>10 mM histidine<br>234 mM sucrose<br>75 ppm Tween 80<br>30 mM arginine<br>pH 5.5 |
| PH6LCARG | 50 mg/ml aTFPI Ab<br>10 mM histidine<br>234 mM sucrose<br>75 ppm Tween 80<br>50 mM arginine<br>pH at 6 |
| PH6LCARG_L | 100 mg/ml aTFPI Ab<br>10 mM histidine<br>234 mM sucrose<br>75 ppm Tween 80<br>30 mM arginine<br>pH 6 |
| 3% STWN80 | 100 mg/ml aTFPI Ab<br>10 mM histidine<br>88 mM sucrose<br>75 ppm Tween 80<br>30 mM arginine<br>133 mM glycine<br>pH 5.5 |
| 3% STWN20_L | 100 mg/ml aTFPI Ab<br>10 mM histidine<br>88 mM sucrose<br>75 ppm Tween 20<br>30 mM arginine<br>133 mM glycine<br>pH 5.5 |
| 3% STWN20_H | 100 mg/ml aTFPI Ab<br>10 mM histidine<br>88 mM sucrose<br>200 ppm Tween 20<br>30 mM arginine<br>133 mM glycine<br>pH at 5.5 |
| 5.5ARG10 | 100 mg/ml aTFPI Ab<br>10 mM histidine<br>88 mM sucrose<br>75 ppm Tween 80<br>10 mM arginine<br>133 mM glycine<br>pH 5.5 |
| 5.5ARG10MET | 100 mg/ml aTFPI Ab<br>10 mM histidine<br>88 mM sucrose |

TABLE 1-continued

| Anti-TFPI Antibody Formulations | |
|---|---|
| Formulation Designation | Formulation Composition |
| | 75 ppm Tween 80<br>10 mM arginine<br>10 mM methionine<br>133 mM glycine<br>pH 5.5 |
| 5.5LYS30 | 100 mg/ml aTFPI Ab<br>10 mM histidine<br>88 mM sucrose<br>75 ppm Tween 80<br>30 mM lysine<br>133 mM glycine<br>pH 5.5 |
| PH5.5HCARGMET | 100 mg/ml aTFPI Ab<br>10 mM histidine<br>234 mM sucrose<br>75 ppm Tween 80<br>30 mM arginine<br>10 mM methionine<br>pH 5.5 |

Each of these anti-TFPI mAb formulations was analyzed by HPLC-SEC for protein aggregation and degradation, LC-MS for aTFPI structural changes (glycation and oxidation), and nephlometry for turbidity assessment, viscometer for viscosity measurement, and osmolality instrument for osmolality measurement. The results for these analyses are presented in Table 2.

TABLE 2

| Osmolality and Viscosity of Anti-TFPI Antibody Formulations | | |
|---|---|---|
| Formulation Composition | Viscosity at 22° C. (mPa-S) | Osmolality (mmol/kg) |
| aTFPI 50 mg/ml<br>Histidine 10 mM<br>Sucrose 234 mM<br>Tween 80 75 ppm<br>pH 5.5 | 1.8 | 272 |
| aTFPI 50 mg/ml<br>Histidine 10 mM<br>Sucrose 234 mM<br>Tween 80 75 ppm<br>pH 5.5<br>Arginine 30 mM | 1.6 | 339 |
| aTFPI 100 mg/ml<br>Histidine 10 mM<br>Sucrose 234 mM<br>Tween 80 75 ppm<br>pH 5.5<br>Arginine 30 mM | 2.9 | 335 |
| aTFPI 50 mg/ml<br>Histidine 10 mM<br>Sucrose 234 mM<br>Tween 80 75 ppm<br>pH 6.0<br>Arginine 50 mM | 2.3- | 373 |
| aTFPI 100 mg/ml<br>Histidine 10 mM<br>Sucrose 234 mM<br>Tween 80 75 ppm<br>pH 6.0<br>Arginine 30 mM | 4.6 | 353* |
| aTFPI 100 mg/ml<br>Histidine 10 mM<br>Sucrose 88 mM<br>Tween 80 75 ppm<br>pH 5.5<br>Arginine 30 mM<br>Glycine 133 mM | 4.1 | 282* |

TABLE 2-continued

| Osmolality and Viscosity of Anti-TFPI Antibody Formulations | | |
|---|---|---|
| Formulation Composition | Viscosity at 22° C. (mPa-S) | Osmolality (mmol/kg) |
| aTFPI 100 mg/ml<br>Histidine 10 mM<br>Sucrose 88 mM<br>Tween 20 75 ppm<br>pH 5.5<br>Arginine 30 mM<br>Glycine 133 mM | 4.5 | 282 |
| aTFPI 100 mg/ml<br>Histidine 10 mM<br>Sucrose 88 mM<br>Tween 20 200 ppm<br>pH 5.5<br>Arginine 30 mM<br>Glycine 133 mM | 4.5 | 278 |
| aTFPI 100 mg/ml<br>Histidine 10 mM<br>Sucrose 88 mM<br>Tween 80 75 ppm<br>pH 5.5<br>Arginine 10 mM<br>Glycine 133 mM | — | 263* |
| aTFPI 100 mg/ml<br>Histidine 10 mM<br>Sucrose 88 mM<br>Tween 80 75 ppm<br>pH 5.5<br>Arginine 10 mM<br>Methionine 10 mM<br>Glycine 133 mM | — | 268* |
| aTFPI 100 mg/ml<br>Histidine 10 mM<br>Sucrose 88 mM<br>Tween 80 75 ppm<br>pH 5.5<br>Lysine 30 mM<br>Glycine 133 mM | — | 288* |
| aTFPI 100 mg/ml<br>Histidine 10 mM<br>Sucrose 234 mM<br>Tween 80 75 ppm<br>pH 5.5<br>Arginine 30 mM<br>Methionine 10 mM | 3.0 | 341 |

*Estimated osmolality based on calculations

Example 3

The Effect of Arginine on Anti-TFPI Ab Glycation

The Example demonstrates that anti-TFPI Ab formulations containing arginine exhibit reduced antibody glycation as compared to anti-TFPI Ab formulations without added arginine.

Anti-TFPI Ab formulations, with and without arginine, at pH 6 were stored at 40° C. for 14 days and tested by LC-MS. The results presented in Table 3 demonstrate that the positively-charged amino acid arginine reduces glycation of anti-TFPI Ab, possibly due to the unique structure of aTFPI Ab, to the level found in a reference standard.

TABLE 3

| Arginine Reduces Anti-TFPI mAb Glycation | | |
|---|---|---|
| Formulation Designation | Formulation Composition | LC-MS Profile |
| PH6.0 | 20 mg/ml aTFPI mAb<br>30 mM Histidine | Glycation |

TABLE 3-continued

| Arginine Reduces Anti-TFPI mAb Glycation | | |
|---|---|---|
| Formulation Designation | Formulation Composition | LC-MS Profile |
| | 292 mM Sucrose<br>100 ppm Tween 80<br>pH 6.0 | |
| 6ARG | 20 mg/ml aTFPI mAb<br>30 mM Histidine<br>292 mM Sucrose<br>100 ppm Tween 80<br>50 mM Arginine<br>pH 6.0 | Comparable to Reference Standard |

It can be concluded based on the results of this study that the stability of aTFPI Ab is highly impacted by formulation pH and the optimum pH for the stability of the formulation is between pH 5 and pH 6 when IV, IM and subcutaneous injection are considered. Arginine appeared to be able to prevent aTFPI Ab glycation. The formulation development and stability studies presented in Example 4 and Example 5 were designed based on these findings.

Example 4

Stability of Anti-TFPI Ab Formulations

The HPLC-SEC results and the LC-MS results of anti-TFPI Ab formulations are summarized in Tables 4-7.

TABLE 4

| Stability of Anti-TFPI Ab Lyophilization Formulations after 3 Months at 5° C. | | |
|---|---|---|
| Formulation Composition | HPLC-SEC Average rate of aggregation formation (%/day)[2] | LC-MS (3 month) |
| aTFPI 50 mg/ml<br>Histidine 10 mM<br>Sucrose 234 mM<br>Tween 80 75 ppm<br>pH 5.5 | 0 | Y |
| aTFPI 50 mg/ml<br>Histidine 10 mM<br>Sucrose 234 mM<br>Tween 80 75 ppm<br>pH 5.5<br>Arginine 30 mM | 0 | Y |
| aTFPI 100 mg/ml<br>Histidine 10 mM<br>Sucrose 234 mM<br>Tween 80 75 ppm<br>pH 5.5<br>Arginine 30 mM | 0 | Y |
| aTFPI 50 mg/ml<br>Histidine 10 mM<br>Sucrose 234 mM<br>Tween 80 75 ppm<br>pH 6.0<br>Arginine 50 mM | 0 | Y |
| aTFPI 100 mg/ml<br>Histidine 10 mM<br>Sucrose 234 mM<br>Tween 80 75 ppm<br>pH 6.0<br>Arginine 30 mM | 0 | Y* |
| aTFPI 100 mg/ml<br>Histidine 10 mM<br>Sucrose 88 mM<br>Tween 80 75 ppm<br>pH 5.5 | 0 | Y* |

TABLE 4-continued

| Stability of Anti-TFPI Ab Lyophilization Formulations after 3 Months at 5° C. | | |
|---|---|---|
| Formulation Composition | HPLC-SEC Average rate of aggregation formation (%/day)[2] | LC-MS (3 month) |
| Arginine 30 mM<br>Glycine 133 mM | | |
| aTFPI 100 mg/ml<br>Histidine 10 mM<br>Sucrose 88 mM<br>Tween 20 75 ppm<br>pH 5.5<br>Arginine 30 mM<br>Glycine 133 mM | 0[1] | Y[1] |
| aTFPI 100 mg/ml<br>Histidine 10 mM<br>Sucrose 88 mM<br>Tween 20 200 ppm<br>pH 5.5<br>Arginine 30 mM<br>Glycine 133 mM | 0[1] | Y[1] |

[1]The calculation was based on 2 month value.

[2]If the rate is negative, zero was entered.

Y: Comparable to the reference standard

Y*: Comparable to the reference standard, with minor modification

TABLE 5

| Stability of Anti-TFPI Ab Lyophilization Formulations after 3 Months at 40° C. | | |
|---|---|---|
| Formulation Composition | HPLC-SEC Average rate of aggregation formation (%/day)[2] | LC-MS (3 month) |
| aTFPI 50 mg/ml<br>Histidine 10 mM<br>Sucrose 234 mM<br>Tween 80 75 ppm<br>pH 5.5 | 0.01 | Glycated |
| aTFPI 50 mg/ml<br>Histidine 10 mM<br>Sucrose 234 mM<br>Tween 80 75 ppm<br>pH 5.5<br>Arginine 30 mM | 0 | Y |
| aTFPI 100 mg/ml<br>Histidine 10 mM<br>Sucrose 234 mM<br>Tween 80 75 ppm<br>pH 5.5<br>Arginine 30 mM | 0.01 | Y |
| aTFPI 50 mg/ml<br>Histidine 10 mM<br>Sucrose 234 mM<br>Tween 80 75 ppm<br>pH 6.0<br>Arginine 50 mM | 0 | Y |
| aTFPI 100 mg/ml<br>Histidine 10 mM<br>Sucrose 234 mM<br>Tween 80 75 ppm<br>pH 6.0<br>Arginine 30 mM | 0.01 | Y* |
| aTFPI 100 mg/ml<br>Histidine 10 mM<br>Sucrose 88 mM<br>Tween 80 75 ppm<br>pH 5.5<br>Arginine 30 mM<br>Glycine 133 mM | 0.01 | Y* |
| aTFPI 100 mg/ml<br>Histidine 10 mM | 0.04[1] | Y[1] |

TABLE 5-continued

| Stability of Anti-TFPI Ab Lyophilization Formulations after 3 Months at 40° C. | | |
|---|---|---|
| Formulation Composition | HPLC-SEC Average rate of aggregation formation (%/day)[2] | LC-MS (3 month) |
| Sucrose 88 mM<br>Tween 20 75 ppm<br>pH 5.5<br>Arginine 30 mM<br>Glycine 133 mM | | |
| aTFPI 100 mg/ml<br>Histidine 10 mM<br>Sucrose 88 mM<br>Tween 20 200 ppm<br>pH 5.5<br>Arginine 30 mM<br>Glycine 133 mM | 0.04[1] | Y[1] |

[1]The calculation was based on 2 month value.
[2]If the rate is negative, zero was entered.
Y: Comparable to the reference standard
Y*: Comparable to the reference standard, with minor modification

TABLE 6

| Liquid Formulations at 5° C. for 3 Months | | |
|---|---|---|
| Formulation Composition | HPLC-SEC Average rate of aggregation formation (%/day)[2] | LC-MS (3 month) |
| aTFPI 50 mg/ml<br>Histidine 10 mM<br>Sucrose 234 mM<br>Tween 80 75 ppm<br>pH 5.5 | 0 | Y |
| aTFPI 50 mg/ml<br>Histidine 10 mM<br>Sucrose 234 mM<br>Tween 80 75 ppm<br>pH 5.5<br>Arginine 30 mM | 0 | Y |
| aTFPI 100 mg/ml<br>Histidine 10 mM<br>Sucrose 234 mM<br>Tween 80 75 ppm<br>pH 5.5<br>Arginine 30 mM | 0 | Y |
| aTFPI 50 mg/ml<br>Histidine 10 mM<br>Sucrose 234 mM<br>Tween 80 75 ppm<br>pH 6.0<br>Arginine 50 mM | 0 | Y |
| aTFPI 100 mg/ml<br>Histidine 10 mM<br>Sucrose 234 mM<br>Tween 80 75 ppm<br>pH 6.0<br>Arginine 30 mM | 0.01 | Y* |
| aTFPI 100 mg/ml<br>Histidine 10 mM<br>Sucrose 88 mM<br>Tween 80 75 ppm<br>pH 5.5<br>Arginine 30 mM<br>Glycine 133 mM | 0.01 | Y* |
| aTFPI 100 mg/ml<br>Histidine 10 mM<br>Sucrose 88 mM<br>Tween 20 75 ppm<br>pH 5.5<br>Arginine 30 mM<br>Glycine 133 mM | 0[1] | Y[1] |

TABLE 6-continued

| Liquid Formulations at 5° C. for 3 Months | | |
|---|---|---|
| Formulation Composition | HPLC-SEC Average rate of aggregation formation (%/day)[2] | LC-MS (3 month) |
| aTFPI 100 mg/ml<br>Histidine 10 mM<br>Sucrose 88 mM<br>Tween 20 200 ppm<br>pH 5.5<br>Arginine 30 mM<br>Glycine 133 mM | 0[1] | Y[1] |
| aTFPI 100 mg/ml<br>Histidine 10 mM<br>Sucrose 88 mM<br>Tween 80 75 ppm<br>pH 5.5<br>Arginine 10 mM | 0 | Y* |
| aTFPI 100 mg/ml<br>Histidine 10 mM<br>Sucrose 88 mM<br>Tween 80 75 ppm<br>pH 5.5<br>Arginine 10 mM<br>Methionine 10 mM | 0 | Y* |
| aTFPI 100 mg/ml<br>Histidine 10 mM<br>Sucrose 88 mM<br>Tween 80 75 ppm<br>pH 5.5<br>Lysine 30 mM | 0.01 | Y* |

[1]The calculation was based on 2 months value.
[2]If the rate is negative, zero was entered.
Y: Comparable to the reference standard
Y*: Comparable to the reference standard, with minor modification

TABLE 7

| Liquid Formulations at 40° C. for 3 Months | | |
|---|---|---|
| Formulation Composition | HPLC-SEC Average rate of aggregation formation (%/day) | LC-MS (3 month) |
| aTFPI 50 mg/ml<br>Histidine 10 mM<br>Sucrose 234 mM<br>Tween 80 75 ppm<br>pH 5.5 | 0.17 | Glycated |
| aTFPI 50 mg/ml<br>Histidine 10 mM<br>Sucrose 234 mM<br>Tween 80 75 ppm<br>pH 5.5<br>Arginine 30 mM | 0.02 | Y* |
| aTFPI 100 mg/ml<br>Histidine 10 mM<br>Sucrose 234 mM<br>Tween 80 75 ppm<br>pH 5.5<br>Arginine 30 mM | 0.04 | Y* |
| aTFPI 50 mg/ml<br>Histidine 10 mM<br>Sucrose 234 mM<br>Tween 80 75 ppm<br>pH 6.0<br>Arginine 50 mM | 0.03 | Y* |
| aTFPI 100 mg/ml<br>Histidine 10 mM<br>Sucrose 234 mM<br>Tween 80 75 ppm<br>pH 6.0<br>Arginine 30 mM | 0.04 | Y* |

TABLE 7-continued

| Liquid Formulations at 40° C. for 3 Months | | |
|---|---|---|
| Formulation Composition | HPLC-SEC Average rate of aggregation formation (%/day) | LC-MS (3 month) |
| aTFPI 100 mg/ml<br>Histidine 10 mM<br>Sucrose 88 mM<br>Tween 80 75 ppm<br>pH 5.5<br>Arginine 30 mM<br>Glycine 133 mM | 0.04 | Y* |
| aTFPI 100 mg/ml<br>Histidine 10 mM<br>Sucrose 88 mM<br>Tween 20 75 ppm<br>pH 5.5<br>Arginine 30 mM<br>Glycine 133 mM | 0.04[1] | Y*[1] |
| aTFPI 100 mg/ml<br>Histidine 10 mM<br>Sucrose 88 mM<br>Tween 20 200 ppm<br>pH 5.5<br>Arginine 30 mM<br>Glycine 133 mM | 0.040[1] | Y*[1] |
| aTFPI 100 mg/ml<br>Histidine 10 mM<br>Sucrose 88 mM<br>Tween 80 75 ppm<br>pH 5.5<br>Arginine 10 mM | 0.07 | Y* |
| aTFPI 100 mg/ml<br>Histidine 10 mM<br>Sucrose 88 mM<br>Tween 80 75 ppm<br>pH 5.5<br>Arginine 10 mM<br>Methionine 10 mM | 0.06 | Y* |
| aTFPI 100 mg/ml<br>Histidine 10 mM<br>Sucrose 88 mM<br>Tween 80 75 ppm<br>pH 5.5<br>Lysine 30 mM | 0.06 | Y* |

[1]The calculation was based on 2 month value.
Y: Comparable to the reference standard
Y*: Comparable to the reference standard, with minor modification

What is claimed is:

1. A salt-free anti-TFPI antibody formulation, comprising:

a. 10 mM to 30 mM histidine, b. 50 ppm to 200 ppm of a non-ionic surfactant, c. 88 mM to 292 mM of a sugar or sugar alcohol selected from mannitol, dextrose, glucose, trehalose and sucrose, d. 10 mM to 50 mM arginine, e. 0 mM to 50 mM lysine, f. 0 mM to 133 mM glycine or alanine g. 0 mM to 10 mM methionine, and h. 1 mg/ml to 150 mg/ml of anti-TFPI human $IgG_2$ antibody having a light chain comprising the amino acid sequence of SEQ ID NO: 1 and a heavy chain comprising the amino acid sequence of SEQ ID NO:2, and wherein said anti-TFPI antibody formulation has a pH of pH 4.0 to pH 6.0, and wherein said anti-TFPI antibody formulation contains substantially no inorganic salt.

* * * * *

SEQUENCE LISTING

```
<160> NUMBER OF SEQ ID NOS: 2

<210> SEQ ID NO 1
<211> LENGTH: 212
<212> TYPE: PRT
<213> ORGANISM: Homo sapiens

<400> SEQUENCE: 1

Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Trp Ser Ser Thr Pro Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190
```

Cys Gln Val Thr His Glu Gly Ser Thr Val Glu Lys Thr Val Ala Pro
195 200 205

Thr Glu Cys Ser
210

<210> SEQ ID NO 2
<211> LENGTH: 442
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Asp Trp Val Arg Gln Ala Pro Gly Lys Gly Leu Glu Trp Val
35 40 45

Ser Ser Ile Arg Gly Ser Arg Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Tyr Arg Tyr Trp Phe Asp Tyr Trp Gly Gln Gly Thr Leu
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Asn
180 185 190

Phe Gly Thr Gln Thr Tyr Thr Cys Asn Val Asp His Lys Pro Ser Asn
195 200 205

Thr Lys Val Asp Lys Thr Val Glu Arg Lys Cys Cys Val Glu Cys Pro
210 215 220

Pro Cys Pro Ala Pro Pro Val Ala Gly Pro Ser Val Phe Leu Phe Pro
225 230 235 240

Pro Lys Pro Lys Asp Thr Leu Met Ile Ser Arg Thr Pro Glu Val Thr
245 250 255

Cys Val Val Val Asp Val Ser His Glu Asp Pro Glu Val Gln Phe Asn
260 265 270

Trp Tyr Val Asp Gly Val Glu Val His Asn Ala Lys Thr Lys Pro Arg
275 280 285

Glu Glu Gln Phe Asn Ser Thr Phe Arg Val Val Ser Val Leu Thr Val
290 295 300

Val His Gln Asp Trp Leu Asn Gly Lys Glu Tyr Lys Cys Lys Val Ser
305 310 315 320

Asn Lys Gly Leu Pro Ala Pro Ile Glu Lys Thr Ile Ser Lys Thr Lys
325 330 335

Gly Gln Pro Arg Glu Pro Gln Val Tyr Thr Leu Pro Pro Ser Arg Glu

-continued

```
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440
```